United States Patent [19]

Fleiszig et al.

[11] Patent Number: 5,948,815
[45] Date of Patent: Sep. 7, 1999

[54] METHODS FOR INHIBITING BACTERIAL CYTOTOXICITY

[75] Inventors: Suzanne M. J. Fleiszig; David J. Evans, both of Berkeley, Calif.

[73] Assignee: The Regents of the University of California, Oakland, Calif.

[21] Appl. No.: 09/042,377

[22] Filed: Mar. 13, 1998

Related U.S. Application Data

[60] Provisional application No. 60/040,721, Mar. 14, 1997.
[51] Int. Cl.[6] .......................... A61K 31/35; A61K 38/16; A61K 31/70
[52] U.S. Cl. ................................ 514/456; 514/6; 514/34
[58] Field of Search ................................ 514/456, 6, 34

[56] References Cited

PUBLICATIONS

Sandros et al. Cellular Events concurrent with Porphyromonas Gingivalis Invasion of Oral Epithelium In Vitro. Europ. J. Oral Sci. 1996 vol. 104, pp. 363–371, see abst.

Ralph et al. Resistance of Melanoma Cell Lines to Interferons Correlates with Reduction of IFN–Induced Tyrosine Phosphorylation: Induction of the Anti–Viral State by IFN is Prevented by Tyrosine Kinase Inhibitors. J. Immunol. 1995, vol. 154, No. 5, pp. 2248–2256, see abst.

Valentin–Weigand et al. Characterization of Group B Streptococcal Invasion in HEP–2 Epithelial Cells. FEMS Microbiol. Letters. Feb. 1997. Vo. 147, pp. 69–75, esp. p. 70, $2^{nd}$ col.

Bandyukova et al., Chemical Abstract 108:71937 (1987) copy of abstract.

Windholz et al. *The Merck Index* (1983) abstracts Nos. 937, 4251, and 9318.

*Primary Examiner*—Kevin E. Weddington
*Attorney, Agent, or Firm*—Richard Aron Osman

[57] ABSTRACT

The invention provides methods and compositions for reducing microbial cytotoxicity to a cell, by contacting a cell subject to extracellular microbial cytotoxicity with an effective amount of at least one of genistein or a genistein derivative. In preferred embodiments, the microbe is a gram-negative bacterium, a non-Enterobacteriaceae or a Pseudomonas aeruginosa or cepacia and the host cell is a mammalian epithelial cell, especially a lung epithelial cell or a corneal epithelial cell. The genistein or genistein derivative may be administered prophylactically prior to infection, subsequent thereto and/or in conjunction with conventional antibiotic therapies.

9 Claims, No Drawings

METHODS FOR INHIBITING BACTERIAL CYTOTOXICITY

CROSS-REFERENCE TO RELATED APPLICATION

This application is a continuing application under 35USC120 of U.S. Ser. No. 60/040,721 filed Mar. 14, 1997, the specification of which is incorporated by reference.

The research carried out in the subject application was supported in part by grants from the National Institutes of Health. The government may have rights in any patent issuing on this application.

INTRODUCTION

1. Field of the Invention

The invention relates to methods for inhibiting bacterial cytotoxicity.

2. Background

Genistein is a well-known isoflavone, naturally derived from soybeans in a glycosolated form known as genistin. It is being studied as a potential chemotherapeutic antitumor drug and is known to be an inhibitor of several protein tyrosine kinases (PTKs). Because of their frequent role in signal transduction, investigators of bacterial invasion have reported the ability of PTK inhibitors, including genistein, to block bacterial uptake by mammalian cells.

Pseudomonas aeruginosa is a Gram-negative bacterial pathogen which causes serious infections in humans when immunity is compromised. *P. aeruginosa* is a leading cause of infectious keratitis, often associated with extended wear of hydrophilic contact lenses, and in which corneal ulceration may lead to scarring and vision loss[1]. This pathogen also causes life-threatening respiratory infections; in patients in hospital intensive care[2], patients with cystic fibrosis[3], and with AIDS[4]. We have found that clinical isolates of *P. aeruginosa* express distinct phenotypes; either invasive (enter and survive in mammalian cells), or cytotoxic (damage or kill mammalian cells).[5,6,7] The two phenotypes are genetically distinct at the chromosomal loci encoding exoenzyme S, yet both phenotypes are virulent in various animal models of respiratory and corneal infections.[7,8,9,10,11] We have developed in-vitro assay systems to study the molecular mechanisms involved in *P. aeruginosa* cytotoxicity and invasion of cells.

In recent years, it has become clear that bacterial cell-mammalian cell interactions involve extensive communication (signaling) between and within cells. Mammalian cell association, invasion, and cytotoxicity by bacterial pathogens can involve the activation, or inhibition, of different signal transduction pathways in the host mammalian cells.[12,13,14] Studies have shown that drugs which inhibit mammalian cell signal transduction proteins prevent cell invasion by some bacterial pathogens.[15,16,17] Genistein, an inhibitor of protein tyrosine kinase (PTK) activity in mammalian cells, is one example[15]. Our own results have shown that entry into corneal epithelial cells by some *P. aeruginosa* strains involves the host cell cytoskeleton and PTK activity[18]. Here we demonstrate that genistein can inhibit cytotoxicity of corneal epithelial cells by *P. aeruginosa*.

Cited Literature

1. Schein O D, et al. N Engl J Med. 1989; 321: 773–778.
2. Chevret S, Hemmer M, Carlet J, Langer M. Intensive Care Med. 1993;19: 256–264.
3. Hoiby N. In: Dodge J A, et al. eds. Cystic Fibrosis—Curr Topics Vol 1. John Wiley & Sons LTD; 1993: 251–268.
4. Dropulic L K, et al. J Infect Dis. 1995; 171: 930–937.
5. Fleiszig S M J, et al. Infect Immun. 1996; 64: 2288–2294.
6. Vallas V, et al. ARVO Abstracts. Invest Ophthalmol Vis Sci. 1996; 37: S870.
7. Fleiszig S M J, et al. Infect Immun. 1997; 65: 579–586.
8. Fleiszig S M J, et al. Infect Immun. 1994; 62: 3485–3493.
9. Kudoh I, et al. Am J Physiol (Lung Cell Mol Physiol. 11). 1994; 267: L551–L556.
10. Tang H, Kays M, Prince A. Infect Immun. 1995; 63: 1278–1285.
11. Preston M J, et al. Infect Immun. 1995; 63: 3497–3501.
12. Bliska J B, Galan J E, Falkow S. Cell. 1993; 73: 903–920.
13. Rosenshine I, Finlay B B. BioEssays. 1993; 15: 17–24.
14. Chen Y, Zychlinsky A. Microbial Pathogenesis. 1994; 17: 203–212.
15. Rosenshine I, Duronio V, Finlay B B. Infect Immun. 1992; 60: 2211–2217.
16. Pace J, Hayman M J, Galan J E. Cell. 1993; 72: 505–514.
17. Ireton K, et al. Science. 1996; 274: 780–782.
18. Fleiszig S M J, Zaidi T S, Pier G B. Infect Immun. 1995; 63: 4072–4077.
19. Fleiszig S M J, Efron N, Pier G B. Invest Ophthalmol Vis Sci. 1992; 33: 2908–2916.
20. Okamoto S, et al. ARVO Abstracts. Invest Ophthalmol Vis Sci. 1993; 34: S1010.
21. Jumblatt M M, Neufeld A H. Invest Ophthalmol Vis Sci. 1983; 24: 1139–1143.
22. Isberg R R, Falkow S. Nature 1985; 317: 262–264.
23. Akiyama T, et al. J Biol Chem. 1987; 262: 5592–5595.
24. Apodaca G, et al. Infect Immun. 1995; 63: 1541–1551.
25. Uehara Y, et al. Biochem Biophys Res Corn. 1989; 63: 803–809.
26. June C H, et al. Proc Natl Acad Sci USA 1990; 87: 7722–7726.
27. Spinozzi F, et al. Leukemia Research. 1994; 18: 431–439.
28. Steller H. Mechanisms and genes of cellular suicide. Science. 1995; 267: 1445–1449.
29. Wilson S E, et al. Invest Ophthalmol Vis Sci. 1996; 37: 1582–1592.
30. Anel A, et al. Eur J Immunol. 1994; 24: 2469–2476.
31. Chen L M, Kaniga K, Galan J E. 1996; 21: 1101–1115.
32. Zychlinsky A, Prevost M C, Sansonetti P J. Nature. 1992; 358:167–169.
33. Khelef N, Zychlinsky A, Guiso N. Infect Immun. 1993; 61: 4064–4071.
34. Monack, D M, et al. Proc Natl Acad Sci USA. 1996; 93: 9833–9838.

Rosenshine et al. (1992) Infection and Immunity 60, 2211–2217 report that genistein can block invasion of HeLa cells by *Yersinia enterocolitica*, and a modified *E. coli* carrying a *Yersinia enterocolitica* invasion gene, but not by *Salmonella typhimurim*. In another report, Fleiszig et al (1995) Infection and Immunity 63, 4072–4077 report that genistein can block invasion of corneal epithelial cells by *Pseudomonas aeruginosa*.

SUMMARY OF THE INVENTION

The invention provides methods and compositions for reducing microbial cytotoxicity to a cell, by contacting a cell subject to extracellular microbial cytotoxicity with an effective amount of at least one of genistein or a genistein derivative. In a particular embodiment, the cell is subject to microbial cytotoxicity by a microbe that induces cytotoxicity without entering the cell. A wide variety of microbes are amendable to cytotoxicity inhibition including unicellular fungi, protists, a viruses and especially, bacteria. In a particular embodiment, the targeted microbes are non-invasive to, and preferably incapable of invading (e.g. the microbe expresses a cytotoxicity gene and such expression renders the microbe incapable of invading), the cell. In preferred embodiments, the microbe is a gram-negative bacterium, a non-Enterobacteriaceae or a *Pseudomonas aeruginosa* or cepacia and the host cell is a mammalian epithelial cell, especially a lung epithelial cell or a corneal epithelial cell. The genistein or genistein derivative may be administered prophylactically prior to infection or subsequent thereto.

In a particular embodiment, the methods involve a first step of ascertaining the suitability of genistein treatment. Such step may be determining the presence of cytotoxicity or a cytotoxic microbe, the presence of a microbial strain associated with cytotoxicity, such as a cytotoxic strain of *Pseudomonas aeruginosa*, the presence of antibiotic resistance or multi-drug resistance, etc.

In a particular embodiment, the genistein or genistein is administered in combination or conjunction with one or more conventional antibiotic therapies. For example, with ocular *Pseudomonas aeruginosa* infection, genistein may be advantageously administered in conjunction with antibiotic cocktails comprising fortified tobramycin and cetazolin, or fortified gentimycin and bacitracin, see, e.g. Onofrey, B. E. Ed. 1991, Clinical Optometric Pharmacology and Therapeutics, esp. Chapter 25. Bacterial Corneal Ulcers.

As used herein, genistein derivatives are intended to include only glycosylated forms of genistein such as genistin, and other modified forms of genistein, or genistein analogs, which forms and analogs inhibit microbial cytotoxicity as described herein for genistein, preferably by effecting a mammalian cell signaling pathway to reduce extracellularly induced bacterial cytotoxicity, by the same structural and functional mechanism as does genistein. Preferred compounds are made by made by subjecting genistein to established chemical derivatizations known in the pharmaceutical arts for optimizing or altering drug action and screening resultant derivatives as described below.

Compositions of the invention include devices for delivering genistein or a genistein derivative to an eye, e.g. an eye medication dispenser, such as an eye dropper, containing a sterile solution comprising at least one of genistein or a genistein derivative. In addition the invention includes solutions of at least one of genistein or a genistein derivative specifically formulated for eye administration such as a sterile solution comprising at least one of genistein or a genistein derivative and an eye medication, a contact-lens reagent, etc.

Composition of the invention also include devices for delivering genistein or a genistein derivative to a lung epithelium, e.g. a lung medication dispenser, such as an inhaler, containing a sterile solution comprising at least one of genistein or a genistein derivative. In addition, the invention includes solutions specifically formulated for lung administration such as a sterile solution of at least one of genistein or a genistein derivative and a lung medication.

Composition of the invention also include devices for delivering genistein or a genistein derivative to a wound, e.g. a wound dressing, a bandage, wound closure (such as suture, etc.), etc., comprising at least one of genistein or a genistein derivative. In addition, the invention includes mixtures specifically formulated for wound administration, particularly topical wound administration, such as a sterile solution of at least one of genistein or a genistein derivative and skin salve, ointment, antibiotic, etc.

The following experiments and examples are offered by way of illustration of particular embodiments or demonstrations of the invention and not by way of limitation.

EXAMPLES

Preparation of Bacteria. Two nonmucoid human corneal isolates of *P. aeruginosa* were used in this study; the cytotoxic serogroup O11 strain 6206[5], and the noncytotoxic serogroup O6 strain 6294 which can invade, and then replicate, in corneal epithelial cells[8, 18] Both of these strains are virulent in an animal model for corneal infection[11]. Bacteria were grown on a Trypticase soy agar plate overnight at 37° C.[19].

Culture of Corneal Epithelial Cells. Immortalized rabbit corneal epithelial cells[20] were grown in 96-well tissue culture plates (Corning, New York, N.Y.) as previously described[5]. Cells were fed with modified SHEM[21], but containing bovine pituitary extract (5 $\mu$g/ml) in place of cholera toxin. Cells used in these experiments were grown for between 3 and 7 days after passaging. Results presented in this study reflect data obtained from cells grown between passages 3 and 10.

Inhibitors. Inhibitors were dissolved in dimethyl sulfoxide (DMSO; Fisher Scientific, Pittsburgh, Pa.) and stored at $-20°$ C. Stock solution concentrations were as follows; genistein (20 mM), herbimycin A (500 $\mu$M), and cytochalasin D (1 mM). Genistein (a protein tyrosine kinase inhibitor) and cytochalasin D (an inhibitor of actin polymerization, hence actin microfilament activity) were obtained from Sigma (St Louis, Mo.). Herbimycin A (a Src-family specific protein tyrosine kinase inhibitor) was obtained from Calbiochem (La Jolla, Calif.).

Before exposure to bacteria, corneal cells were treated with genistein (200 $\mu$M, 1 h), herbimycin A (5 $\mu$M, 3.5 h), or cytochalasin D (10 $\mu$M, 1 h). Since the drug stock solutions contained DMSO, matching concentrations of DMSO were added to control samples without treatment drugs. In most experiments, the cells were incubated with bacteria in the continued presence of the drug for treated samples. In some experiments, as noted in the text, the drug was not added during the incubation of bacteria with cells; only cells were pretreated with drug. In other experiments, only the bacteria were pretreated with drugs. Bacterial and cell viability in the presence of each drug was monitored in control samples that were included in every experiment. None of the drugs tested affected bacterial viability or growth (as assessed by standard bacterial viable counts), nor did they affect corneal cell viability (as assessed by trypan blue staining).

Measurement of Cytotoxicity. Trypan blue exclusion assays were used to measure the cytotoxic effects of *P. aeruginosa* strain 6206 on a rabbit corneal epithelial cell line[5]. Trypan blue stains the nucleic acids of dead or dying cells when significant disruption of plasma membrane integrity has occurred. Experiments were performed in MEM (Minimal Essential Medium Eagle, with Earle's salts and L-glutamine; Cellgro™, Mediatech, from Fisher Scientific). Briefly, the cytotoxic *P. aeruginosa* strain (6206) was resuspended in pre-warmed (37° C.) MEM to a concentration of $2 \times 10^6$ cfu/ml. Corneal epithelial cells were washed once with MEM (100 $\mu$l), exposed to inhibitor or control solutions in MEM (100 $\mu$l), and then incubated with 100 $\mu$l of bacterial suspension ($\sim 2 \times 10^5$ bacteria) with or without inhibitors for 3 h (37° C., 5% $CO_2$, pH 7.4). Bacterial suspensions were then removed from all samples, and cells were treated with 200 $\mu$l gentamicin solution (200 $\mu$g/ml) (Biowhittaker, Walkersville, Md.) for 1.5 h to kill extracellular bacteria. This was done to match the methods used for invasion assays described below, and to prevent progression of cytotoxicity beyond the 3 h incubation period. After washing once with MEM (200 $\mu$l) to remove gentamicin, 100 $\mu$l trypan blue solution (0.04%w/v) (Sigma) was added for 15 min to visualize dead or dying cells.

Measurement of Bacterial Invasion of Cells. Bacterial invasion was assessed by gentamicin survival assays[22]. The methods used were similar to the cytotoxicity experiments described above, but with three modifications: 1) the invasive *P. aeruginosa* strain 6294 was used rather than the cytotoxic strain 6206, 2) cells were inoculated with a smaller inoculum of $\sim 2 \times 10^4$ cfu, and 3) after killing extracellular bacteria with gentamicin treatment, cells were washed once with MEM (200 $\mu$l), then lysed with 100 $\mu$l triton X-100 (0.25% v/v) (Sigma). The number of viable intracellular bacteria was determined by viable counts of the cell lysate.

Effect of Protein Tyrosine Kinase Inhibitors on *P. aeruginosa* Cytotoxicity. Genistein, a potent inhibitor of mammalian cell PTK activity[23], prevented the cytotoxic effects of *P. aeruginosa* strain 6206 on the corneal cells. Without genistein treatment, significant bacterial-induced cytotoxicity occurred, as illustrated by the many areas (foci) of trypan blue staining. This was typical of *P. aeruginosa* induced cytotoxicity described previously in primary cultures of corneal epithelia[5], and in other cell types[7, 24]. In the genistein treated group, little trypan blue staining was observed, there were only a few dead cells, and the epithelium was intact with no foci of cytotoxicity present. A similar outcome was observed in eight other experiments performed under the same conditions.

Trypan blue exclusion assays can be used either as a qualitative method of assessing cytotoxicity, or as a semi-quantitative method, by scoring cytotoxicity with a grading scale where 1=no cytotoxicity, and 4=massive cytotoxicity. In previous studies, results obtained with the semi-quantitative method have correlated closely with a chromium release quantitative method[5]. In this study, we made a quantitative determination of *P. aeruginosa* cytotoxicity using photographs of trypan blue stained corneal epithelia. Photographs were divided into equal quadrants, and the number of dead cells per quadrant counted. There were significantly fewer dead cells in the genistein treated epithelia vs. control untreated samples (p=0.0001) (Table 1).

Herbimycin A, like genistein, inhibits PTK activity in mammalian cells, although it is more specific for the Src-family of PTK's.[25, 26] In similar experiments to those described above, corneal epithelial cells were exposed to *P. aeruginosa* strain 6206 in the presence or absence of herbimycin A. In contrast to genistein, herbimycin A did not prevent bacterial-induced cytotoxicity (p=0.38) (Table 1).

TABLE 1

Effect of PTK Inhibitors on Cytotoxicity Induced by *P. aeruginosa* Strain 6206

| Treatment | Number of affected cells (trypan blue stained)[‖] | |
|---|---|---|
| | Control[§] | Treated |
| Genistein (200 $\mu$M)* | 468 ± 44 | 79 ± 2 (p = 0.0001) |
| Herbimycin A (5 $\mu$M)[†] | 339 ± 66 | 314 ± 50 (p = 0.38) |
| Genistein (200 $\mu$M)[‡] (cell pretreatment only) | 241 ± 27 | 174 ± 15 (p = 0.04) |

*Cells were pretreated with genistein for 1 h and then the drug was also added during incubation with bacteria.
[†]Cells were pretreated with herbimycin A for 3.5 h and then the drug was also added during incubation with bacteria.
[‡]Cells were only pretreated with genistein (for 1 h).
[§]Cells were not treated with drug
[‖]Expressed as mean (± standard error) number of affected cells per quadrant (area $\sim 4 \times 10^5 \mu m^2 \sim 4000$ epithelial cells). Statistical significance assessed using an unpaired t-test.

We explored whether genistein prevented *P. aeruginosa*-induced cytotoxicity through an effect on the host corneal cells or through an action on the bacteria. Table 1 includes the results of an experiment in which corneal epithelial cells were pretreated with genistein, but genistein was not added during the incubation with bacteria, i.e. bacteria were not exposed to genistein. The pretreatment of cells with genistein reduced cytotoxicity (p=0.04) (Table 1), although this effect was not as great as when the drug was present for the entire time that the cells were incubated with bacteria. These results indicate that genistein inhibits cytotoxicity via a reversible effect on the mammalian cells, and that the host cell participates in *P. aeruginosa*-induced cytotoxicity.

Protein Tyrosine Kinase Activity and *P. aeruginosa* Invasion. The effect of genistein and herbimycin A on invasion of *P. aeruginosa* into the immortalized rabbit corneal epithelial cells was tested. Cells were exposed to the invasive *P. aeruginosa* strain 6294 in the presence or absence of genistein or herbimycin A. Both PTK inhibitors reduced invasion of *P. aeruginosa* strain 6294 into these corneal cells. Genistein reduced bacterial invasion by 96%, and herbimycin A by 58%, as compared to untreated control epithelia in the same series of experiments (p<0.05, ANOVA). These experiments were repeated twice with similar results.

Inhibition of 6294 invasion by genistein, similar to protection against strain 6206 cytotoxicity, was found to be reversible, and occurred through an action on the corneal cells. In an experiment in which bacteria were pretreated with genistein, before being incubated with the corneal cells in the absence of the drug, pretreated bacteria were incubated with either untreated corneal cells (control), or cells which had also been pretreated with genistein. Results showed that only pretreating bacteria with genistein, i.e. no corneal cell treatment, did not significantly inhibit invasion (p>0.05, ANOVA). However, P. aeruginosa invasion was inhibited by 46% (p<0.05, ANOVA) when pretreated bacteria were exposed to cells which had also been pretreated with genistein. This result is consistent with other studies[15] which have shown genistein has a smaller effect on invasion when drug treatment of cells is not continued throughout the assay, and again demonstrates the reversibility of the actions of genistein.

Prevention of P. aeruginosa Cytotoxicity is Not Due to Inhibition of Invasion. Herbimycin A inhibited 6294 invasion, but not 6206 cytotoxicity, indicateing that P. aeruginosa 6206 may not need to enter the corneal cells in order to kill them. Therefore, we explored the cytotoxic activity of strain 6206 in the presence of another drug that inhibits bacterial invasion by a different mechanism.

Cytochalasin D blocks invasion of various types of bacteria by inhibiting actin microfilament activity[13,17]; this drug blocked P. aeruginosa invasion of primary cultured rabbit corneal epithelia[18]. In this study, we established that cytochalasin D also inhibits P. aeruginosa invasion of immortalized rabbit corneal epithelia (by 96%, p<0.05, ANOVA) using the noncytotoxic invasive strain 6294. Although cytotoxic strains are generally considered to be noninvasive, they do demonstrate low levels of background epithelial cell invasion (residual invasion)[5]. Using an inoculum 10-fold higher than for experiments with the invasive strain, residual invasion by the cytotoxic strain 6206 was 287±82 (mean±standard error) for untreated cells, and only 3±3 for cytochalasin D treated cells (99% inhibition). Residual invasion of this cytotoxic strain was also reduced by genistein (13±7; 95% inhibition), and by herbimycin A (110±35; 62% inhibition) (p<0.05, ANOVA). These data indicate that corneal cell entry mechanisms of invasive and cytotoxic P. aeruginosa strains are similar.

Rather than preventing the cytotoxic activity of strain 6206, cytochalasin D caused a consistent and dramatic increase in the susceptibility of corneal cells to bacterial killing. Control samples, in which cells were only pretreated with the drug, showed that increased susceptibility to cytotoxicity occurred via an effect on corneal epithelial cells, and not on the bacteria. Cytochalasin D did not cause strain 6294 to become cytotoxic.

Cytotoxicity towards mammalian cells is thought to be a pathogenic mechanism of many types of bacteria, including P. aeruginosa.[5, 7, 9, 14, 24] Our results show that corneal epithelial cell damage caused by a cytotoxic strain of P. aeruginosa could be prevented by genistein. The dose of genistein which blocked cytotoxicity (200 μM) inhibits PTK activity in other mammalian cells[27], indicateing a role for PTK in cytotoxicity mediated by this pathogen. Reversibility of the effects of genistein in our experiments is consistent with reversible effects of this drug on PTK activity[23]. The Src-family of PTK does not appear to be involved in P. aeruginosa-induced corneal cytotoxicity, since herbimycin A did not prevent bacterial-induced cell death.

Other studies have shown that cytotoxicity by some bacteria involves necrosis and/or apoptosis of mammalian cells[14]. For P. aeruginosa, it is not clear which of these mechanisms is involved in the cytotoxic effects of this pathogen, since there was microscopic evidence for both apoptosis and necrosis in MDCK cells exposed to a cytotoxic P. aeruginosa strain PA103[24]. The Fas system (Fas and Fas ligand) represents one of several cellular pathways leading to a final common pathway for induction of apoptosis[28]. This system is present in corneal epithelia[29]. If apoptosis is involved in P. aeruginosa cytotoxicity towards corneal epithelia, then it is unlikely to be through Fas ligand induction. Fas ligand induction can be blocked by both genistein and herbimycin A by inhibition of Src-family PTK activity[30]. Our results show that herbimycin A did not reduce P. aeruginosa cytotoxicity towards corneal epithelial cells. In contrast, P. aeruginosa invasion was inhibited by herbimycin A indicateing that entry of P. aeruginosa into corneal cells involves Src-PTK activity.

Both herbimycin A and cytochalasin D inhibited P. aeruginosa invasion, but not cytotoxicity. These results indicate that invasion is not a prerequisite for P. aeruginosa-induced cell death. Indeed, doses of cytochalasin D that prevented P. aeruginosa invasion actually enhanced cytotoxicity. This is in direct contrast to several other invasive bacterial pathogens. Cytochalasin D does not enhance cytotoxicity of macrophages by Salmonella spp.[31]. For both Shigella flexneri,[32] and Bordetella pertussis,[33] bacterial induced apoptosis in macrophages is reduced by cytochalasin D. For these pathogens invasion may be a prerequisite for cytotoxicity. Salmonella typhimurium may also exhibit invasion-dependent cytotoxicity, since non-invasive mutants of S. typhimurium cannot kill macrophages[31, 34].

Pseudomonas aeruginosa Invasion and Cytotoxicity are Independent Events, Both Involving Protein Tyrosine Kinase Activity. P. aeruginosa clinical isolates exhibit invasive or cytotoxic phenotypes. Cytotoxic strains acquire some of the characteristics of invasive strains when a regulatory gene, exsA, that controls the expression of several extracellular proteins, is inactivated. ExsA mutants are not cytotoxic and can be detected within epithelial cells by gentamicin survival assays. To determine if epithelial cell invasion precedes and/or is essential for cytotoxicity, we measured invasion (gentamicin survival) and cytotoxicity (trypan blue staining) of PA103 mutants deficient in specific exsA-regulated proteins, and tested the effect of drugs that inhibit invasion for their effect on cytotoxicity. A transposon mutant in the exsA-regulated extracellular factor exoU, was neither cytotoxic nor invasive. Furthermore, several of the drugs that inhibited invasion did not prevent cytotoxicity. These results show that invasion and cytotoxicity are mutually exclusive events, inversely regulated by an exsA encoded invasion inhibitor(s). Both involve host cell protein tyrosine kinase (PTK) activity, but differ in that invasion requires Src-family tyrosine kinases and calcium-calmodulin activity. PTK inhibitor drugs such as genistein are shown to have therapeutic potential through their ability to block both invasive and cytotoxicity pathways via an action on the host cell.

In vivo efficacy of genistein treatment of Pseudomonas aeruginosa ocular infection. The efficacy of genistein and genistein-antibiotic combination therapies was tested in animal models essentially as described by Preston, M. J., et al. 1995, Infection and Immunity. 63: 3497–3501. Briefly, six week old female mice were anesthetized and subjected to three corneal epithelial scratches (Preston et al., 1995). Left eyes were innoculated with 5×10⁶. Pseudomonas aerugi-

*nosa* (cytotoxic strain 6206). After 5 hrs rest, the eyes were treated every 2 hrs for up to 24 hrs post-infection. Treatments included genistein at 200 $\mu$M in PBS in a 5 $\mu$l drop; gentimycin at 14 mg/ml in PBS in a 5 $\mu$l drop; a combination of genistein at 200 $\mu$M and gentimycin at 14 mg/ml in PBS in a 5 $\mu$l drop; and a control of a 5 $\mu$l drop of PBS. After 24 hrs, the mice were killed and the eyes photographed and graded for infection. We found grade 3 infection in all untreated mice; 80% grade 1 and 20% grade 0 in the gentimycin treated mice; and 75% grade 0 and 25% grade 1 in the combination treated mice. Furthermore, microscopic examination revealed significant corneal protection in the genestein and combination treated mice. In further experiments, we found significant grade reductions in genistein treated mice as compared with control mice.

All publications and patent applications cited in this specification are herein incorporated by reference as if each individual publication or patent application were specifically and individually indicated to be incorporated by reference. Although the invention is described in some detail by way of illustration and example for purposes of clarity of understanding, it will be readily apparent to those of ordinary skill in the art in light of the teachings of this invention that certain changes and modifications may be made hereto without departing from the spirit or scope of the following claims.

What is claimed is:

1. A method for reducing microbial cytotoxicity to a mammalian cell, the method comprising the steps of:

(a) determining that the cell is subject to microbial cytotoxicity by a microbe that induces cytotoxicity without entering said cell; and
   (b) contacting the cell with an effective amount of at least one of genistein or a genistein derivative, whereby the microbial cytotoxicity to the cell is reduced.

2. A method according to claim 1, wherein the microbe is a cytotoxic unicellular fungi, a protist, a viruses or a bacterium.

3. A method according to claim 1, wherein the microbe is a cytotoxic gram-negative bacterium.

4. A method according to claim 1, wherein the microbe is a cytotoxic non-Enterobacteriaceae.

5. A method according to claim 1, wherein the microbe is a cytotoxic *Pseudomonas aeruginosa* or *cepacia*.

6. A method according to claim 1, wherein the cell is a mammalian epithelial cell.

7. A method according to claim 1, wherein the cell is a mammalian epithelial cell selected from a lung epithelial cell and a corneal epithelial cell.

8. A method according to claim 1, wherein the contacting step further comprises contacting the cell with an effective amount of an antibiotic composition.

9. A method according to claim 1, wherein said microbe is a cytotoxic *Pseudomonas aeruginosa* or *cepacia*, the cell is a corneal epithelial cell and the contacting step further comprises contacting the cell with an effective amount of an antibiotic composition comprising at least one of tobramycin, cetazolin, gentamycin and bacitracin.

* * * * *